United States Patent [19]

Sanderson

[11] 4,449,003

[45] May 15, 1984

[54] PROCESS FOR THE PRODUCTION OF BIS(4-HYDROXYPHENYL)BIPHENYL DISULFONE

[75] Inventor: John R. Sanderson, Austin, Tex.

[73] Assignee: Mobay Chemical Corporation, Pittsburgh, Pa.

[21] Appl. No.: 364,828

[22] Filed: Apr. 2, 1982

[51] Int. Cl.$^3$ .................. C07D 147/06; C07D 147/10
[52] U.S. Cl. ...................................................... 568/33
[58] Field of Search ........................................ 568/33

[56] References Cited

U.S. PATENT DOCUMENTS 3,269,986 8/1966 Goldberg .............................. 260/49
3,402,204 9/1968 Plummer et al. ...................... 568/33

FOREIGN PATENT DOCUMENTS 54-39074 3/1979 Japan ...................................... 568/33
56-22761 3/1981 Japan ...................................... 568/33
56-71062 6/1981 Japan ...................................... 568/33

OTHER PUBLICATIONS

"Cleavage of Alkyl Aryl Ethers with Lithium Iodide", by I. T. Harrison, J. Chem. Soc. D 1969 (11), p. 616.

*Primary Examiner*—Paul M. Coughlan, Jr.
*Assistant Examiner*—D. B. Springer
*Attorney, Agent, or Firm*—Gene Harsh; Lawrence S. Pope; Aron Preis

[57] ABSTRACT

The present invention relates to a process for the production of bis(4-hydroxyphenyl)biphenyl disulfone.

6 Claims, No Drawings

PROCESS FOR THE PRODUCTION OF BIS(4-HYDROXYPHENYL)BIPHENYL DISULFONE

BACKGROUND OF THE INVENTION

Bis(4-hydroxyphenyl)biphenyl disulfone has been found to be a useful monomer in preparing polymers such as polyurethanes, polycarbonates, polyethers, polyesters and polysulfones. Polycarbonates prepared using such a monomer are disclosed in U.S. Pat. No. 3,269,986. Such polymers are generally useful in films, fibers, injection molded parts, extruded tubes and molded parts, blow molded articles and coatings. The art is noted to include the note entitled "Cleavage of Alkyl Aryl Ethers with Lithium Iodide" by I. T. Harrison, J. Chem. Soc. D 1969 (11), p. 616.

The object of the present invention is to provide a novel process for the preparation of bis(4-hydroxyphenyl)biphenyl disulfone.

SUMMARY OF THE INVENTION

The present invention pertains to a process for the preparation of bis(4-hydroxyphenyl)biphenyl disulfone comprising reacting 4,4'-biphenyldisulfonylchloride with anisole in the presence of a catalyst to produce bis(4-methoxyphenyl)biphenyl disulfone and refluxing the bis(4-methoxyphenyl)biphenyl disulfone in the presence of a lithium halide.

DETAILED DESCRIPTION OF THE INVENTION

The process of the present invention can be illustrated by the following general reaction scheme:

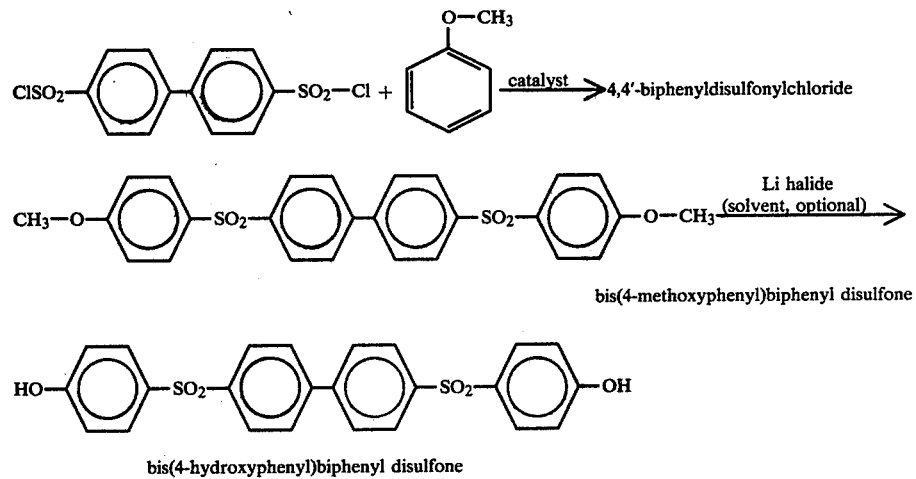

Suitable catalysts are Lewis acids, preferably FeCl$_3$.

Suitable solvents usable in the process include quinoline, pyridine, trimethylpyridine and dimethylformamide (DMF). Preferably, quinoline is used.

Suitable lithium halides include lithium iodide, lithium chloride and lithium bromide. Preferably, lithium iodide is used.

This process for the preparation of bis(4-hydroxyphenyl)biphenyl disulfone is advantageous because mild conditions are used in the Fridel-Crafts reaction resulting in less by-product formation. Furthermore, the process of the invention produces yields of bis(4-hydroxyphenyl)biphenyl disulfone of from about 60 to 80%.

The invention will be further illustrated, but is not intended to be limited, by the following example.

EXAMPLE 4,4'-diphenyldisulfonylchloride (35.1 g, 0.10 mol), anisole (200 ml) and ferric chloride (2.0 g) were placed in a 500 ml flask equipped with a stirrer, thermometer, condenser and nitrogen purge. The reaction mixture was heated to 40°–45° C. for 17 hours. The solid was collected with suction, washed with dilute HCl and then with acetone. The solid was recrystallized three times from dimethylformamide (mp 268°–271° C.). A Nuclear Magnetic Resonance spectrum (in trifluoroacetic acid) showed the correct ratio of aromatic to aliphatic protons. The presence of only one isomer was indicated since there was only a single sharp peak for methoxy.

Bis(4-methoxyphenyl)biphenyl disulfone (5.0 g), lithium iodide monohydrate (5.0 g) and 50 ml quinoline were placed in a 100 ml flask and refluxed for 4 hours. The reaction mixture was poured into ethyl acetate and extracted with 10% HCl (4 times with 100 ml) and H$_2$O (1 time with 100 ml). The ethyl acetate solution was dried over sodium sulfate and removed on a rotating evaporator to yield 6.7 g of bis(4-hydroxyphenyl)biphenyl disulfone. This solid still contained some quinoline, and thin layer chromatography indicated the presence of 20% bis(methoxyphenyl)biphenyl disulfone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of bis(4-hydroxyphenyl)biphenyl disulfone comprising the steps of (i) reacting 4,4'-biphenyldisulfonylchloride with anisole in the presence of a Lewis acid as catalyst to produce bis(4-methoxyphenyl)biphenyl disulfone and (ii) isolating the reaction product (iii) refluxing the bis(4-methoxyphenyl)biphenyl disulfone in the presence of a lithium halide to produce said bis(4-hydroxyphenyl)biphenyl disulfone and (iv) isolating the reaction product of (iii).

2. The process of claim 1 wherein said refluxing is carried out in a solvent.

3. The process of claim 1 or 2 wherein said Lewis acid is $FeCl_3$.

4. The process of claim 2 wherein said solvent is DMF.

5. The process of claim 2 wherein said solvent is quinoline.

6. The process of claim 1 or 2 wherein said lithium halide is lithium iodide.

* * * * *